United States Patent [19]

Lindstrom et al.

[11] Patent Number: 4,695,536
[45] Date of Patent: Sep. 22, 1987

[54] CORNEAL STORAGE SYSTEM

[76] Inventors: Richard L. Lindstrom, 20050 Lakeview Ave., Excelsior, Minn. 55391; Donald J. Doughman, 5228 W. Highwood Dr., Edina, Minn.; Debra Skelnik, P.O. Box 344, Cambridge, Minn. 55008

[21] Appl. No.: 569,609

[22] Filed: Jan. 10, 1984

[51] Int. Cl.$^4$ .............................................. A01N 1/02
[52] U.S. Cl. .................................... 435/1; 435/240.3; 435/240.2
[58] Field of Search ........................... 435/240, 241, 1

[56] References Cited

U.S. PATENT DOCUMENTS 4,282,326  8/1981  Moldenhauer ...................... 435/240
4,443,546  4/1984  Stemerman et al. ................ 435/240

OTHER PUBLICATIONS

Gibco Catalog (1978-1979).
Kaufman et al.-Am. J. of Ophthalmology, Jul. 1984, pp. 112-114.
Recent Advances in Kertoplasty with Special Reference to the Advantage of Liquid Preservation by Takashi and Reizo Marabe-Folia Ophthalmological Japonica 19(12): 1310-1318, (1968).
Organ Preservation for Transplantation by Karow and Pegg, 1981, pp. 427-441.
Organ Culture Corneal Storage at Ambient Room Temperature, Lindstrom et al., Archives of Ophthalmology, vol. 95, pp. 869-878, May, 1977.
Chondroitin Sulfate in a New Cornea Preservation Medium, Kaufman et al., American Journal of Opthalmology, Jul. 1984, pp. 112-114.

*Primary Examiner*—Sam Rosen
*Attorney, Agent, or Firm*—Hugh D. Jaeger

[57] ABSTRACT

A universal tissue preservation system including a storage container and a preservation media for corneal and other tissue storage. The universal corneal preservation system provides for closed system storage (media not changed) at 4° centigrade under refrigeration for 1-14 days or 34° centigrade storage in an incubator for at least 35 days (five weeks). The storage system provides for a quarantine technique insuring sterility, and a special media for maintaining cell viability and corneal deturgescence, (normal thickness). The corneal storage container provides for endothelial cell photography and media sampling. The preservation media can also be utilized in an open batch technique (media changed at regular intervals) for storage of corneas over one year. In addition, the preservation media can be used as an intraocular irrigation fluid during surgery.

14 Claims, 3 Drawing Figures

CORNEAL STORAGE SYSTEM

BACKGROUND TO THE INVENTION

1. Field of the Invention

The present invention pertains to surgery, and more particularly, pertains to tissue and/or corneal preservation systems for storing corneas or other organs for subsequent transplant.

2. Description of the Prior Art

The prior art systems maintain living cornea tissue in a suspension of death, through freezing or refrigeration. These systems have been less than desirable in that the tissue progressivly looses viability during storage, the tissue has been of questionable sterility, and it has not been adaptable to store the tissue at various and fluctuating temperatures.

Numerous articles have been published regarding organ preservation for transplantations such as that by *Karow and Pegg, Organ Preservation for Transplantation,* 1981. Pages 428–441 were specifically devoted to the "cornea".

Another prior art article devoted to the subject is "Organ Cultural Corneal Storage at Ambient Room Temperature" by Richard L. Lindstrom, M.D., from the Archives of Ophthalmology, May 1077, Volume 95, page 869–878, which delineate the prior art.

The endothelial cell is of primary importance in the maintenance of normal corneal transparency. Since adult human corneal endothelial cells have limited, if any, regenerative capacity, the success of penetrating kertoplasty (corneal transplantation) in humans depends on transplanting an adequate amount of functioning donor endothelium.

Therefore, any method used to store the donor cornea, from the death of the donor to its transplant into the recipient, must maintain endothelial cell viability.

Present methods include refrigeration of the whole globe at 4° centigrade, which results in a progressive loss of endothelial cells at this low temperature. Although the use of TC199 with Dextran (M-K media) at 4° centigrade to store the cornea-scleral segment, may increase the duration of storage to 96 hours, prolonged preservation is again not possible because of progressive endothelial cell death. Cryo preservation allows a storage time of up to at least one year but the complex technology limits its use to a few centers. In addition, a high rate of endothelial cell death in common following tissue thawing.

The present invention overcomes the disadvantages of prior art by providing a universal corneal preservation system, which as a closed system provides for sterility and intermediate to long-term corneal storage. The flexibility and simplicity of the system may be particularly useful in third-world countries.

SUMMARY OF THE INVENTION

The general purpose of the present invention is a universal corneal preservation system which provides for maintaining clear tissue of normal thickness and endothelial cell populations over a period of time, insures stability and control of sterility of the tissue, and is adaptable for short term preservation at temperatures of 4° centegrade, intermediate term storage at room temperature, and long term storage at 34° centigrade. The storage media provides for health of the corneal tissue and provides for maintaining the cornea in a living viable state. Future additives may allow controlled endothelial cell growth providing in effect a "super cornea". The fluid for storage of the media is enriched to assure tissue viability. The fluid can also be utilized for irrigation during intraocular surgery with minimal damage to intraocular cells. The storage media is also applicable for storage of other body tissues or organs.

According to one embodiment of the present invention, there is provided a corneal storage system including a storage media for maintaining viability and corneal deturgescence (normal thickness) of the cornea. A special container supports the cornea in the media while also providing for endotheiial cell photography through the container holding the cornea. The media provides for utilization of storage of the cornea and can also be used as an irrigation fluid during ocular surgery.

The medium includes 500 ml Gibco's minimum essential media (Eagles) with Earls salts, 25 mM HEPES buffer without L-glutamine; 50 ml of decomplemented calf serum of 25 ml of decomplemented calf serum and 25 ml of decomplemented fetal calf serum or 50 ml of decomplemented fetal calf serum as a 10 percent final concentration; 5 ml of L-glutamine (200 mM) at 1 percent final concentration; chondroitin sulfate at 1 percent to 10 percent; antibiotics such as 10,000 units/ml of penicillin plus 50–100 ug/ml of garamycin (plus or minus 0.25 ug/ml of amphotericin B) whereby the solution is equalibrated to 7.2–7.6 pH through 5 percent $CO_2$ and 95 percent air.

According to another embodiment of the present invention, there is provided a support bottle including a suitable stopper which can be penetrated with a needle to obtain cultures, a support such as a stainless steel wire with a hook or alligator clip for hooking an edge of the cornea for suspending the cornea in the media, and a viewing window being provided on one side of the bottle for endothelial cell counting a recessed molded insert for specular microscopy and photography. The bottle includes a specular microscope chamber for zooming into viewing and positioning of the cornea endothelial side upwards with parallel line supports for holding the cornea during the specular microscopy viewing. The vertical supports provide for fluid circulation and support of the cornea during the microscopy viewing.

One significant aspect and feature of the present invention is that the universal corneal storage system provides for closed system storage which allows the cornea or tissue to be preserved at a temperature range from 4° centigrade to 34° centigrade (including quarantine for sterility).

Another significant aspect and feature of the present invention is a container providing for endothelial cell photography, as well as specular microscopy examination.

Further significant aspect and feature of the present invention is a special media to maintain tissue and endothelial cell viability and corneal deturgescence. The cornea can be shipped in this media following storage at 4° centigrade to 34° centigrade in the same container to an eye bank over a minimum of a 24 hour period. The media is also useful as an irrigation fluid during ocular surgery and also for tissue preservation during storage of other organs or during other surgery. The system also allows media change, which provides long term storage of corneas up to a one year period. (The system also provides that the cornea can be shipped to other methods of preservation.)

An additional significant aspect and feature is a system which provides for (bio engineering) during storage such as HLA typing, adding of endothelial cells, encouraging of cell growth, and like biological systematic functions. (The whole eye can also be stored in the media for 3–4 days in storage situations at 4° to 34° centigrade.)

Having thus described embodiments of the present invention, it is a principal object hereof to provide a universal corneal storage system.

One object of the present invention is a universal corneal storage system that allows human donor corneas to be stored in a closed system up to 14 days at 4° centigrade or up to 5 weeks at 34° centigrade prior to transplantation. This corneal storage system at 34° centigrade incorporates a terminal sterility procedure that insures the sterility safety and quality of donor tissue, a media modification for maintenance of corneal deturgescence and a complete tissue processing methodology.

Another object of the present invention is a process for the decontamination of donor globes, the culturing of cornea-scleral rims, a format for checking terminal sterility, a technique of shipping tissue at 4° to 34° centigrade, and a method of testing donor corneal endothelial viability prior to transplantation.

A further object of the present invention is a media which can be utilized as an irrigation fluid during ocular surgery and for the preservation of other tissues and organs.

A further object of the present invention is to provide a universal system which stores the cornea for 2 weeks at 4° centigrade, or 5 weeks or longer at 34° centigrade. The media utilizes chondroitin sulfate to keep the cornea thin at the respective temperatures. The system also provides a quarantine period allowing simultaneous microbial culture to insure sterility.

An additional object of the present invention is flexibility to utilize a closed system for corneal storage up to 5 weeks or an open batch system with media changes for storage up one year. With these media changes, cornea storage can be extended for over one year. The cornea can be shifted from any storage system into the universal storage system of the present invention or vice versa.

DESCRIPTION OF PREFERRED EMBODIMENTS

Corneal Storage Bottle

Figure 2:
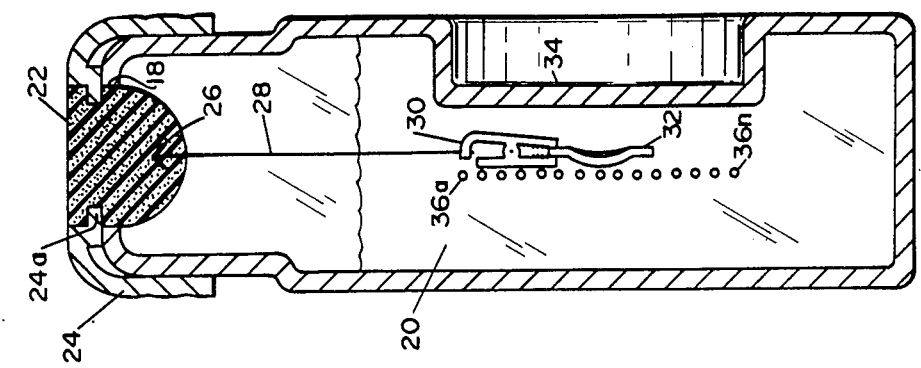
FIG. 2 illustrates a side view of a corneal storage bottle.
Figure 1:
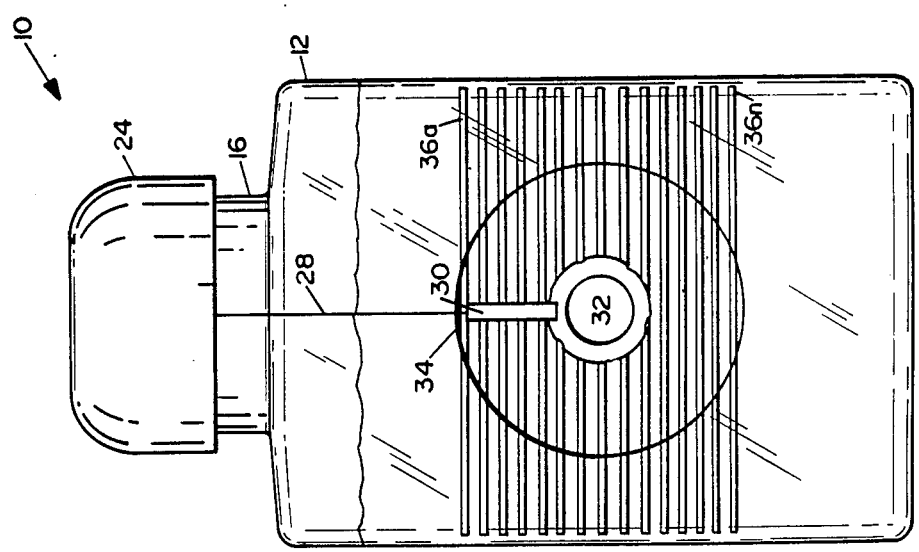
FIG. 1 illustrates a front view of a corneal storage bottle.

FIG. 1 illustrates a front view of the corneal storage container 10 including a general bottle type of configuration such as glass or polymer material 12, and a neck 16 having a mouth 18 with a diameter for accommodating passage of a cornea as also illustrated in FIG. 2. The container 12 is filled with a corneal media 20 as later described in detail. A rubber stopper 22 is provided with a metal crimped seal 24 including circular member 24a securing the stopper 22. The rubber stopper is a type which can be penetrated with a needle to obtain cultures and the like. A hook support hanger 26 includes a stainless steel wire 28 secures into the rubber stopper 22 with an alligator clip 30 at one end for securing the cornea globe 32. The alligator clip, or in alternative a hook, can be stainless steel, prolene material, or PMMA material. The container is provided with a inward indentation 34 for specular microscopy viewing and also for endothelial cell counting. A plurality of dividers 36a–36n are provided opposite the viewing indentation 34 for supporting of the cornea during viewing and also providing for passage and circulation of the fluid within the container.

Figure 3:
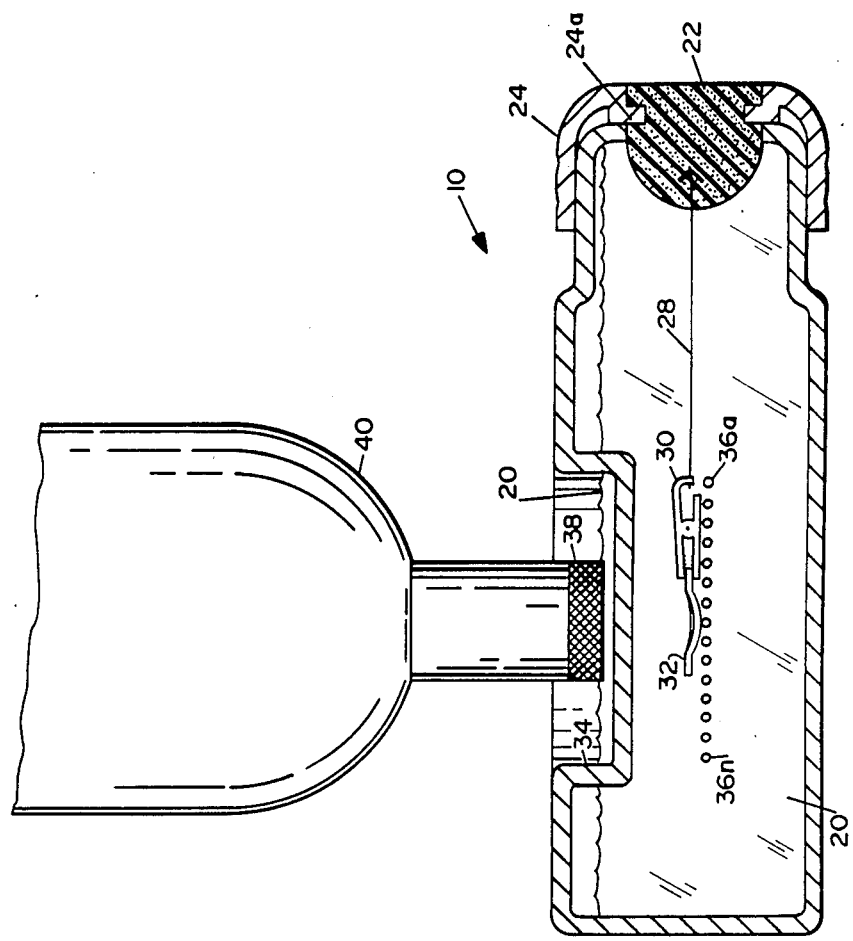
FIG. 3 illustrates a mode of operation of the corneal storage bottle.

FIG. 2 illustrates a side view of the container 12 where all numerals correspond to those elements previously described. During the specular microscopy viewing, the corneal endothelial side is up towards the viewing chamber. The support ribs 36a–36n hold the cornea in position for exact placement with respect to the viewing window for the specular microscopy as illustrated in FIG. 3 where a lens 38 of a microscope 40 is immersed in media fluid 12 in the indentation 34.

Cornea Storage Media

The corneal storage media 20 includes 500 ml Gibco's minimum essential media (Eagles) with Earls salts, 25 mM HEPES buffer without L-gluthamine; 50 ml of decomplemented calf serum or 25 ml of decomplemented calf serum and 25 ml of decomplemented fetal calf serum or 50 ml of decomplemented fetal calf serum as a 10 percent final concentration; 5 ml of L-glutamine (200 mM) at 1 percent final concentration; chondroitin sulfate at 1 percent to 10 percent; antibiotics such as 10,000 units/ml of penicillin plus 50–100 ug/ml of garamycin (plus or minus 0.25 ug/ml of amphotericin B) whereby the solution is equalibreated to 7.2–7.6 pH through 5 percent $CO_2$ and 95 percent air. The Gibco's media is a synthetic media, catalog number 320–1095, manufactured by Grand Island Biological Company.

A key ingredient of the media is the chondroitin sulfate at a 1 to 10 percent concentration, while 1 to 3 percent is preferred. This chondroitin sulfate concentraation provides for the maintenance of corneal deturgescence during storage. Any like high molecular weight molecule can also be utilized accordingly such as glycosaminoglycans, polysaccharides, sodium hyaluronate, keratan sulfate, polyvinyl pyrolidone, methyl cellulose, hydroxy propylmethyl cellulose, cellulose gum, dextran, etc.

The cornea storage system is utilized as follows:

The donor cornea is processed as being received as a whole globe or as a donor cornea-scleral rim. If a whole globe is received, the excess conjunctiva is trimmed. The globe is immersed in a 0.5 percent Betadine solution for 2½ to 3 minutes, rinsed with a sterile saline solution, and then immersed in garamycin 3 mg/cc for 2½ to 3 minutes, then rinsed again with sterile saline for aseptisizing prior to storage. The limbus is cultured again as when the whole globe is received. If a corneal-scleral rim is received, a culture is done at the limbus, but no decontamination is done. If the whole globe is received, the donor corneal-scleral rim is excised taking care not to collapse the anterior chamber.

The cornea is then placed in 15 cc of media for 45 minutes with gentamycin 100 mg/ml or like antibiotic for a prestorage wash. The cornea is then washed or dipped three times in separate 15 cc solutions of the media to remove any contaminates.

The cornea is then placed in a closed system bottle of 100–250 cc of medium at 34° centigrade or 4° centigrade or any temperature there between. Accordingly, either an incubator or refrigerator is required. At the seventh day of storage 10 cc media is removed for culture. (On the seventh day to twenty-first day, the culture is reviewed under a fourteen day quarantine.) On days 21–35 or later the cornea can be removed for use if all cultures are negative. The cornea can then be shipped at 4° or 24° or at any temperature between 4° to 34° for up to 24 hours without damage.

Corneas are processed for either intermediate or long term corneal storage in a closed system at temperature ranges from 4° centigrade to 34° centigrade depending on organ bank needs. Corneas are first received, then decontaminated, and then the corneas undergo a prestorage wash to reduce contaminates.

Corneas are suspended via suture, a wire support, or PMMA through the scleral rim in 100 ml–250 ml volume of media and stored at 4° centigrade for 1 to 14 days or 34° centigrade for at least 5 weeks. Temperature shifts of 34° centigrade to 4° centigrade or room temperature of any temperature between 4° and 34° centigrade are tolerated for up to 24 hours for transportation.

The bottle is a serum type made of Type I glass with 28 mm I.D. mouth. The cap consists of a rubber stopper plus a 2 part aluminum seal which is crimped over the stopper, thereby insuring a tamper-proof, secure closure. This cap permits removal of a media sample by simply removing the outer portion of the aluminum cap and withdrawing media with a syringe and needle through the I.V.-type stopper. The inner portion of the stopper remains crimped over the glass vial.

Current Day Flow Chart

Day 0
  Corneas decontaminated (see below)
Day 0
  Excised corneas placed in open system, rim cultured, with antibiotics in the media for washes.
Day 0
  Corneas transferred to media with antibiotics, closed system or open system.
Day 0
  Corneas are suspended in bottle media with antibiotics, by placing a suture (synthetic, non-absorbable) through the scleral rim and then through the inner lip of the rubber stopper or wire support.
Day 7
  10 ml media sample removed from bottle for microbial evaluation.
Day 7 to Day 21
  Reports received from microbiology on day 7 to 21.
Day 7 to Day 21
  Quarantine for sterility check.
Day 21 to 1 year
  Cornea may be utilized for local transplant or shifted to 4° centigrade or room temperature for shipping to another eye bank or surgeon.

All procedures are carried out using sterile techniques preferably in a laminar flow hood. The tissue culture media presently used in out system is Gibco's Minimum Essential Media (MEM) (Eagles) with Earl salts, 25 mM HEPES buffer without L-glutamine and additives.

Preparation of MEM with antibiotics and anitmycotics

The following things are added to a 500 ml bottle of MEM:
1. 50 ml of decomplemented fetal calf serum or combination=10 percent final concentration or fetal calf serum.
2. 5 ml of L-glutamine (200 mM)=1 percent final concentration.
3. Antibiotics/antimycotics such as GIBCO FORMULA 79-0192
   (a) penicillin 10,000 units/1 ml)
   (b) (amphotericin B 0.25 ug/1 ml)
4. Gentamycin 80 ug/2 cc—add 1.25 cc=50 ug/1 ml final concentration.
5. Chondroitin sulfate to reach 1–10 percent final concentration.

Decomplemented calf serum, L-glutamine, antibiotic/antimycotic solutions should be stored at −20° centigrade. Gentamycin solution should be stored at room temperature.

MEM 500 ml bottles are stored at 4° centigrade.
1. Remove all above solutions from freezer—except gentamycin
   a. Thaw vials and bring up to 31° centigrade, wipe off excess moisture with 70 percent alcohol and gauze pad. Place in hood.
   b. Shake up contents, remove cap. Flame briefly (vials are plastic) and pour into flamed MEM bottle.
   c. Observe sterile procedure for adding in gentamycin: Using alcohol swab, swab top of vial. Insert sterile needle, withdraw 1.25 ml of solution. Put into flamed MEM bottle.
   d. Swirl MEM bottle, reflame bottle and cap, and return bottle to refrigerator when completed. (4° centigrade)

In the handling of the media process the media is always brought up to 31° centigrade or 34° centigrade via a water bath, or by placement in an incubator. The outside of the bottle is always wiped with a 70 percent alcohol gauze pad before placing in the hood. Care is taken when pouring media, and all spills are wiped up. If there is a drop of media on the side of a bottle, it is wiped away with 70 percent alcohol and the bottle is reflamed. The bottle and cap are always flamed after pouring. Label the date, and initial MEM bottle showing whether it contains antibiotics/antimycotics or is without antibiotics/antimycotics.

* Without antibiotics/antimycotics does have 1 percent L-glutamine and 10 percent serum.

Calf serum is supplied by Gibco in a 500 ml bottle, and should be or must be handled under sterile procedure. The bottle should be or must be wiped off on the outside with a 70 percent alcohol swab and placed under the hood. The working area inside the hood should be wiped down with 70 percent alcohol. Flame the bottle, and with a sterile 10 cc pipet, pipet out 10 cc into sterile individually wrapped culture tubes. Place tubes in freezer at −20° centigrade. Sterility check of calf serum: plate out 0.5 cc of calf serum onto Sheep Red Blook plate (SRB) and Sabarands (SAB) plate; date and label plate. Put SRB into 31 degrees centigrade incubator and put SAB plate in container at room temperature, wait 7 days and check to see if there is any contamination of these plates. If there is no contamination, then serum can be used for MEM media.

Antibiotics/Antimycotics: 100 ml bottles are also supplied by Gibco on a special order. Again the bottles are handled under sterile procedures. Wipe off the outside of bottle with 70 percent alcohol swab. Flame the botttle, and with a sterile 10 cc pipet, pipet out 5 ml into sterile tissue culture tube, individually wrapped. Label and place into freezer at $-20°$ centigrade. L-glutamine is the same as antibiotics/antimycotisc—5 ml per tube. Follow the sterilization procedure. When frozen L-glutamine has a white, cloudy appearance, and when thawed the solution becomes clear. Chondroitin sulfate reacts the same at these temperatures.

MK Media contains Gibco's TC-199 with 40,000 MW dextran 10 percent solution with 50 mcg/1 Ml gentamycin. This solution may also be used for shipping corneas or corneas may be transferred from this solution to universal system for longer term preservation.

Implant Procedures

Globes that have been enucleated should be placed in eye bottles with corneas up, and should be rinsed with 5 cc of Garamycin Ophthalmic Solution and place in refrigerator at 4° centigrade. The corneas should be evaluated by slit-lamp examination, and careful evaluation of age, medical history, post mortem time and post-enucleation time. In the slip-lamp examination the cornea is examined for epithelial or stromal pathology, and in particular endothelial disease. The following eye evaluation is recommended for use: (a) Is there evidence of scleral jaundice?; (b) Is the epithelium intact?; (c) Are there stromal opacities?; (d) Grade the amount of stromal edema.; (e) Are there folds in the Descemet's membrane?; (f) Guttata?; (g) Is there evidence of ocular surgery, (e.g., aphakia, pterygium)?

In the handling of globes in the tissue culture lab a technician should wash their hands and arms with 10 percent Betadine Scrub for 3 minutes prior to working in the laminar flow hood. A sterile gown, gloves, and mask should also be worn. Remove the globe from the eye bottle and place on a sterile gauze pad in the laminar flow hood. Remove eye bottle from the hood. Anytime a technician removes his hands from outside of the laminar flow hood the hands should be swabbed with 70 percent alcohol.

When using the pre-washed swab open the tryptic soy broth tube and flame top of the tube. Moisten swab (Calgiswab Type II) with tryptic soy broth and swab 360 degrees around limbus. Insert the swab into the tryptic soy broth tube and break off the end, flame top of the tube and cap (place cap loosely on tube). Label "Prewash" with cornea number. After cornea is planted, place TSB tube in incubator at 31° centigrade.

In the decontamination procedure a technician should maintain a sterile procedure at all times. Trim all conjuctiva and muscle tissue from globe using sterile instruments. Flush globe with normal saline of approximately 24 cc. Pour 10 cc of 5 percent betadine into sterile eye cup and immerse globe for 3 minutes then pour 5 cc of Garamycin Ophthalmic Solution into sterile eye cup and immerse globe for 3 minutes. Each globe has an individual cup and garamycin solution. The area where the globe is to be placed on sterile gauze should be swabbed down with 70 percent alcohol. The globe is removed from garamycin solution with sterile forceps and placed on the sterile gauze pad. The globe is then rinse with 20 cc of sterile saline to remove the residue of garamycin. This is done so that no antibiotic solution comes into contact with the endothelial cells. Now place globe on new sterile gauze pad.

Follow the pre-wash procedure as explained above for the post wash. Label "Post Wash" with cornea number. In a petri dish pour 1 ml per dish of MEM and Antibiotics and bring it up to 34° centigrade. Note: standard media listed under "Media". Sterile procedures used: flame bottle, pour, flame bottle and cap, replace cap.

When removing the cornea use sterile instruments, score sclera with razor blade, including a 2–3 mm rim of sclera. Using an iris scissors very carefully cut around the cornea while gently holding sclera with sterile forceps. When the entire cornea is cut, gently peal off remaining iris or ciliary body. Try not to put any undue stress on cornea. Place the cornea endothelial side up in a petri disch with antibiotics, label the dish with cornea number and date. This is a rinsing step for 45 minutes. After 45 minutes, rinse in three different petri dishes of media, dipping 5 times each. Place cornea endothelial side up in a new sterile dish and put labeled cornea dish into incubator at 34° centigrade with 5 percent $CO_2$ and 100 percent humidity, or place in universal storage system. If there is any spillage against the sides of the petri dish, repeat rinsing procedure and replant in new sterile dish. Record the time and date planted, the cornea number, post-mortem time, post enucleation time and any comments about planting of eyes, ie. condition of cornea, abrasions, discolorations, etc.

If contamination occurs in the system, remove cornea immediately from incubator and record date in book. Streak out one loop full of contaminated media onto sheeps red blood and SAB plates. Sheeps red blood plate should be at 31° and SAB plate at room temperature. When colonies appear, send to microbiology for identification.

If contamination occurs in plates which were plated out, record date and number of cornea in book and check with microbiology to determine if their sample is also contaminated, then send the plates to microbiology for identification. Any contamination should always be recorded and documented.

In the open system the tissue culture media is changed three times weekly. A surgical gown, gloves, and mask should be worn during this procedure. The MEM bottle is warmed up to 34° centigrade, wiped off with a 70 percent alcohol swab, and placed in hood. The petri dishes are placed in hood on tray. Media is carefully removed by a vacuum line attached to a sterile 9 inch glass pipets. Each petri dish is changed with an individual pipet to avoid contamination. Petri dishes are refilled with sterile MEM and the bottles and cap are flamed. All vacuum apparatus is rinsed in a antimicrobial agent.

Some corneas are shifted into the universal system from MK media. MK media=TC-199+40,000 MW Destran+antibiotics. Corneas are sent by air, packed in ice. Each cornea is accompanied by an information card, with age, sex, cause of death, post-enucleation time, and time put into MK. Wipe the outside of the vial with 70 percent alcohol and place in hood. Pour up petri dishes with MEM and A.A. (Media should be pre-warmed to 31° centrigrade) Flame MK vial briefly, with a sterile 10 cc pipet pipet out 15 ml of MK media then tilt vial and remove cornea with sterile forceps grasping the scleral rim only. Transfer cornea into petri dish with MEM, label dish, and put into culture or in universal system. Plate out 0.5 ml of media into SRB, SAB plates and incubate SRB at 31° centigrade and the SAB at room temperature. The MK vial should then be stored at −20° centigrade. Growth may be inhibited because gentamycin is present in media; bacterial but not mycotic contamination. These corneas follow the standard method of quarantine. After storage, corneas may be shipped at 4° to 34° centigrade for up to 24 hours.

We claim:

1. Corneal storage media comprising 500 ml Gibco's minimum essential media (Eagles) with Earls salts, 25 mM HEPES buffer without L-glutamine; 50 ml of decomplemented calf serum or 25 ml of decomplemented calf serum and 25 ml of decomplemented fetal calf serum or 50 ml of decomplemented fetal calf serum at a 10 percent final concentration of final media volume; 5 ml of L-glutamine (200 mM) at 1 percent final concentration of final media volume; chondroitin sulfate at 1 percent of 10 percent to final media volume; and, antibiotics of 10,000 units/ml of penicillin plus 50–100 ug/ml of garamycin (plus or minus 0.25 ug/ml of amphotericin B) whereby the solution is equilibrated to 7.2–7.6 pH through 5 percent $CO_2$ and 95 percent air.

2. Media comprising:
   a. minimum essential media including 500 ml Gibco's minimum essential media with Earls salts, 25 mM HEPES buffer without L-glutamine, 5 ml of L-glutamine at 1 percent final concentration of final media volume and antibiotics including 50–100 ug/ml of garamycin sulfate;
   b. an effective amount of serum from the group of calf serum, fetal calf serum or human serum for allowing intermediate and long terms corneal preservation, and;
   c. an effective amount of a high molecular weight compound selected from the group of chondroitin sulfate, sodium hyaluronate, heparan sulfate, keratan sulfate, dextran or cellulose gum, for maintaining corneal deturgescence during immediate and long term preservation.

3. Media of claim 2 wherein said high molecular weight compound is selected from a group of biodegradable substances of chondroitin sulfate, glycosaminoglycans, or polysaccharides in a 1 to 10 percent concentration of final media volume.

4. Media of claim 2 wherein said high molecular weight molecule is selected from a group of sodium hyaluronate, keratan sulfate, polyvinyl pyrrolidone, methyl cellulose, hydroxy proplymethyl cellulose, cellulose gum, or dextran.

5. Media of claim 2 wherein said high molecular weight molecule is chondroitin sulfate in a 1 to 10 percent concentration of final media volume.

6. Media of claim 5 wherin said concentration is in a 1 to 3 percent range of final media volume.

7. Process of corneal storage comprising:
   a. mixing a corneal storage media including Gibco's minimum essential media of 50 ml essential media with Earls salts, 25 mM HEPES buffer without L-glutamine, 5 ml of L-glutamine (200 mM) at 1 percent final concentration of final media volume and antibiotics including 50–100 ug/ml of garamycin; serum from the group of calf serum, fetal calf serum or human serum; and an effective amount of high molecular weight molecule selected from a group consisting of chondroitin sulfate, sodium hyaluronate, keratan sulfate, sodium hyaluronate, keratan sulfate, polyvinyl-pyrolidone, methyl cellulose, hydroxy-prophylmethylcellulose, cellulose gum and dextran;
   b. filling a corneal storage container with said mixed media; and,
   c. supporting a corneal-scleral rim in said container containing said media whereby said media is kept at a temperature between 4° centigrade to 34° centigrade thereby providing intermediate term storage, and long term storage, and said system allowing shifting of temperature providing for transportation of tissue.

8. Process of claim 7 wherein said high molecular weight molecule is chondroitin sulfate in a 1 to 10 percent concentration is final media volume.

9. Process of claim 8 wherein said concentration is in a 1 to 3 percent range of final media volume.

10. Process of claim 7 wherein said high molecular weight molecule is selected from a group of biodegradable substances of chondroitin sulfate, glycosaminoglycans, or polysaccharides in a 1 to 10 percent concentration of final media volume.

11. Process of claim 7 wherein said media is kept at 4° C. for eye-bank storage.

12. Process of claim 7 wherein said media is kept at 34° C.

13. Intraocular media comprising 500 ml Gibco's minimum essential media (Eagles) with Earls salts, 25 mM HEPES buffer without L-glutamine; ten percent fetal bovine serum; 5 ml of L-glutamine 200 mM at 1 percent final concentration of final media volume; chondroitin sulfate at 1–3 percent of final media volume; an effective amount of antibiotics, the solution being equilibrated to 7.2–7.6 pH through 5 percent $CO_2$ and 95 percent air.

14. Intraocular media comprising 500 ml Gibco's minimum essential media (Eagles) with Earls salts, 25 mM HEPES buffer without L-glutamine; ten percent fetal decomplemented calf serum; 5 ml of L-glutamine at 1 percent final concentration of final media volume; chondroitin sulfate at 1–35 percent of final media volume; and, an effective amount of antibiotics, the solution being equilibrated to 7.2–7.6 pH through 5 percent $CO_2$ and 95 percent air for corneal storage of living tissue.

* * * * *